United States Patent [19]

Ng

[11] Patent Number: 4,974,593

[45] Date of Patent: Dec. 4, 1990

[54] HOLDER APPARATUS FOR TRANSDUCER APPLICABLE TO HUMAN BODY

[76] Inventor: Raymond C. Ng, 1737 Oak Grove, San Marino, Calif. 91108

[21] Appl. No.: 441,042

[22] Filed: Nov. 24, 1989

[51] Int. Cl.[5] ............................................. A61B 5/04
[52] U.S. Cl. ................................. 128/639; 128/644; 128/775; 128/780
[58] Field of Search ..................... 128/639–641, 128/643–644, 774–775, 778, 780, 782, 798, 802–803, 672, 662.03–662.04

[56] References Cited

U.S. PATENT DOCUMENTS

| Re. 28,990 | 10/1976 | Hon et al. . |
| 3,367,323 | 2/1968 | Schuler . |
| 3,379,901 | 4/1968 | Richards . |
| 3,520,294 | 7/1970 | Fuzzell et al. . |
| 3,599,628 | 8/1971 | Abbenante et al. . |
| 3,662,743 | 5/1972 | Amarante et al. . |
| 3,703,168 | 11/1972 | Frink . |
| 3,780,725 | 12/1973 | Goldberg . |
| 3,851,320 | 11/1974 | Dahl . |
| 3,859,984 | 1/1975 | Langley . |
| 3,916,878 | 11/1975 | Courtin et al. . |
| 3,989,034 | 11/1976 | Hojaiban . |
| 4,090,504 | 5/1978 | Nathan . |
| 4,459,992 | 7/1984 | Gwyn . |
| 4,640,295 | 2/1987 | Isaacson ........................... 128/775 X |
| 4,696,307 | 9/1987 | Montgieux ....................... 128/721 |
| 4,781,200 | 11/1988 | Baker . |
| 4,785,822 | 11/1988 | Wallace . |
| 4,860,768 | 8/1989 | Hon et al. ....................... 128/775 X |

FOREIGN PATENT DOCUMENTS 2180944 4/1987 United Kingdom ............... 128/672

Primary Examiner—Max Hindenburg
Assistant Examiner—John P. Lacyk
Attorney, Agent, or Firm—William W. Haefliger

[57] ABSTRACT

A monitoring transducer positioning apparatus, for retention to the body of a patient, comprising an inverted generally cup-shaped holder to receive and position the transducer, first structure associated with the holder to retain it to the patient's body, and second structure on the holder to urge the transducer toward the patient's body, relative to the holder.

14 Claims, 1 Drawing Sheet

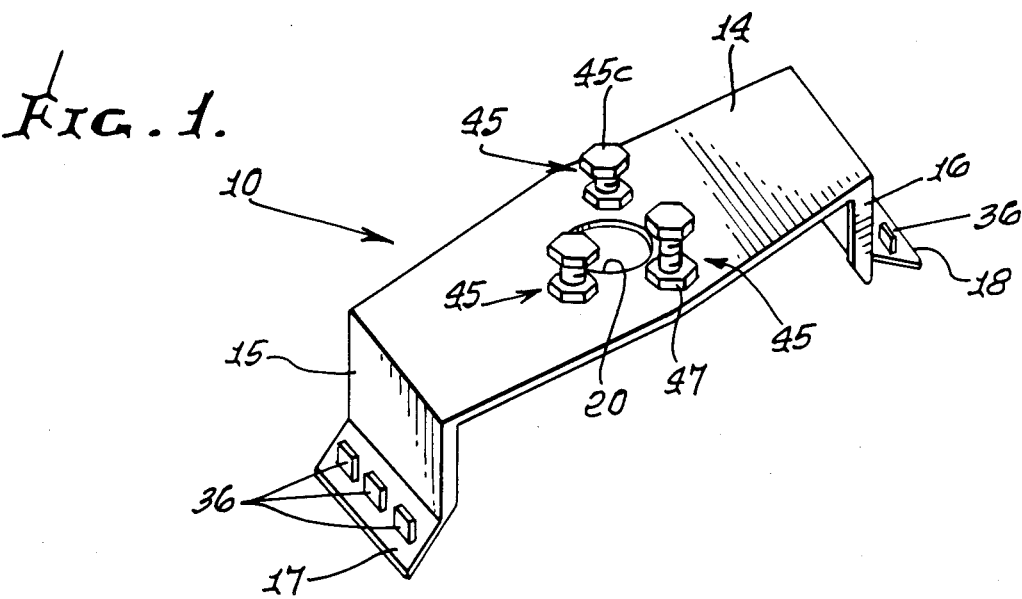
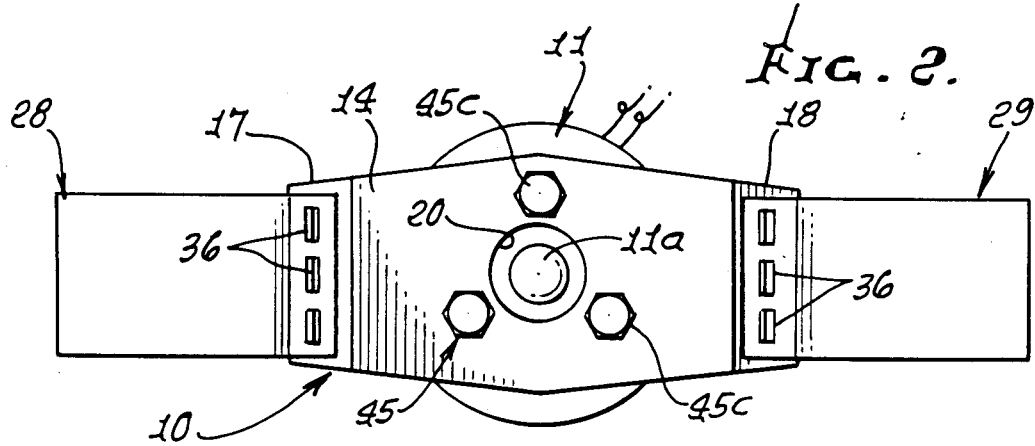
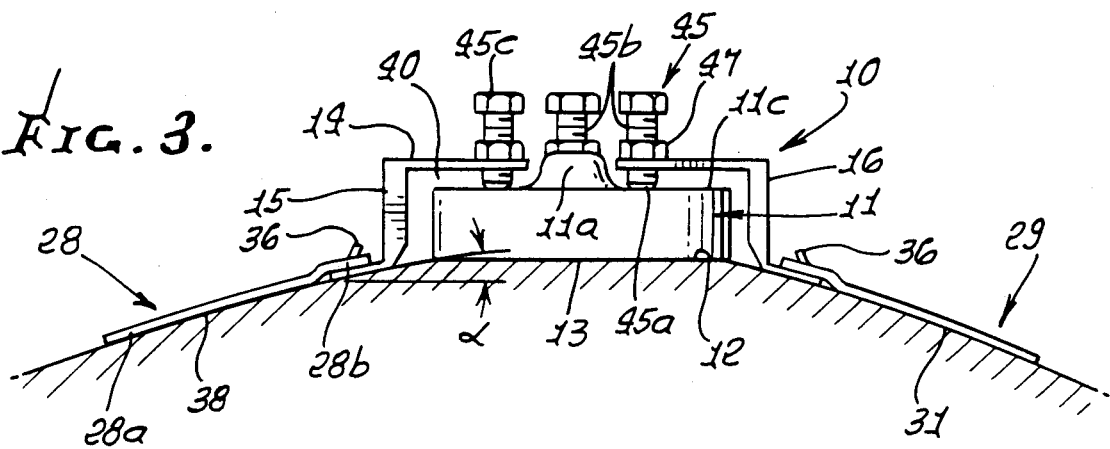
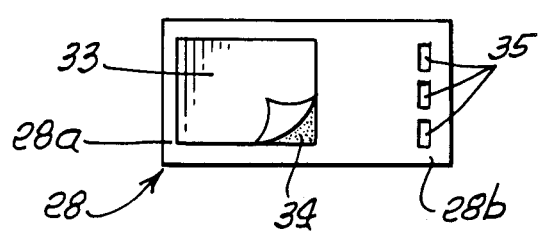

HOLDER APPARATUS FOR TRANSDUCER APPLICABLE TO HUMAN BODY

BACKGROUND OF THE INVENTION

This invention relates generally to monitoring devices; and more particularly concerns the retention of unborn infant heartbeat monitoring transducers, as during labor.

In the past, such transducers were held in position on the enlarged abdomen of a woman in labor as via a strap or straps. The latter were necessarily extended all the way around the woman's back, and were uncomfortable, and difficult to keep in position during the many hours of labor leading up to childbirth. Clearly, there is need for improved means to hold such transducers in position on the abdomen.

SUMMARY OF THE INVENTION

It is a major object of the invention to provide a solution to the above difficulty and problem, to meet the described need.

Basically, the invention comprises monitoring transducer positioning apparatus that comprises
  (a) an inverted generally cup-shaped holder to receive and position the transducer,
  (b) first means associated with the holder to retain it to the patient's body, and
  (c) second means on the holder to urge the transducer toward the patient's body, relative to the holder.

As will appear, the first means as referred to typically includes flange means projecting from the holder, and adapted to removably connect to retainer means that has an adhesive surface applicable to the patient's body. Such retainer means may take the form of a pad having a first portion connectible to the flange means and a second portion defining said adhesive surface. A second portion of the pad typically defines another adhesive surface adhered to the flange means.

It is another object of the invention to provide such flange means in the form of two flanges extending generally oppositely from skirt sections defined by said holder, the flanges being angled to fit the curvature of a pregnant patient's abdomen In this regard, the retainer means then may take the form of two pads, having first portions connectible to the respective flanges, and second portions defining adhesive surfaces applicable to a patient's body. Further, the two flanges and the pad first portions may advantageously have tongue and groove interconnection allowing the pads to be lifted off the flanges for temporary disconnection of the holder from the pads, while the pad second portions remain adhesively secured to the patient's body. Yet another object of the invention is to provide one or more adjustable set screws on the cup-shaped holder, to project into a recess defined by the holder, for urging the transducer toward the patient's body. Three such set screws may be provided, with ends engageable with the transducer at three locations.

The holder itself may include a base and skirt means integral with the base, there being threaded openings carried by the base for threaded reception of the adjustable set screws. The screws are typically carried by nuts on the base and pass through the nuts and the base for engagement with the transducer. The screws are typically spaced about a central through opening in the base, as will appear.

These and other objects and advantages of the invention, as well as the details of an illustrative embodiment, will be more fully understood from the following specification and drawings, in which:

DRAWING DESCRIPTION

FIG. 1 is a perspective view of apparatus incorporating the invention;

FIG. 2 is a plan view of the FIG. 1 apparatus, applied to the abdomen;

FIG. 3 is a side elevation of the FIG. 2 apparatus; and

FIG. 4 is a plan view of a retainer pad as used in FIG. 3.

DETAILED DESCRIPTION

In the drawings, positioning apparatus 10 is provided, for positioning a heartbeat monitoring transducer 11 adjacent the abdomen, such as the enlarged abdomen 12 of a Woman in labor. The transducer under surface 13 must be held firmly against the abdomen in order to properly detect heartbeat pulses of an unborn infant; and the transducer may also be used to detect uterine muscle activities. One such known transducer is manufactured by Hewlett Packard Company.

The apparatus 10 is in the form of an inverted, generally cup-shaped holder having a horizontally elongated base wall 14, two skirt sections 15 and 16 integral with the base wall and extending generally downwardly from the latter, and two flanges 17 and 18 respectively connected to the skirt sections and extending laterally and downwardly, at angles from horizontal to fit the abdomen curvature. These elements may consist of lightweight molded plastic material, so that they define a unitary bracket-type means. The skirts may be regarded as skirt means, and the flanges as flange means.

A central opening 20 in the base wall 14 is adapted to receive an enlargement 11a on the top of the transducer; but opening 20 is not required in the event the transducer does not incorporate such an enlargement. Elements 14–18 are typically quite thin, as for example between 1/14 and ⅛ inches in the plane of the base, as well as generally normal to the planes of the skirt sections.

The flanges 17 and 18 are adapted to removably connect to like pads 28 and 29 which in turn are adapted to be adhesively attached (removably) to the patient's body, as at 30 and 31 in FIG. 3. FIG. 4 shows the underside 28a of a pac 28, with a sheet 33 covering adhesive 34 on the pad. When the sheet 33 is pulled off, the pad is turned over and pressed onto the abdomen to removably attach adhesive 34 to the skin.

Another portion of each pad is connectible to a flange, to hold the flange against the abdomen. See for example portion 28b of pad 28 in FIG. 4, with openings or grooves 35 formed therein Such openings are adapted to receive or pass tongues or projections 36 on the flange 17. Those tongues are angled upwardly and toward the skirt section 15, i.e. away from the pad adhesive portion, to prevent inadvertent loosening of the tongue and groove connections when the pad retains the flange to the abdomen. Conversely, this form of connection allows ready lift-off detachment of the pad from the flange, without pulling the pad adhesive from the skin, whereby the cup-shaped holder and the transducer may be lifted from, i.e. removed from, the patient's abdomen should the patient desire to rise and walk about.

Pad 29 is attached to flange 18 in the same way as pad 28 connects to flange 17; and pad 29 is also adhesively attachable to the patient's abdomen. Such pads may be regarded as within the scope of first means adhesively attachable to the patient's abdomen. Such pads may be regarded as within the scope of first means associated with the holder to retain it to the patient's body.

Second means is also provided on the holder to adjustably urge the transducer toward the patient's body when the pads retain the holder in FIG. 3 position. Such second means typically may include at least one set screw projecting into a recess 40 formed by the holder beneath base wall 14 and between the like skirt sections 15 and 16. As for example, the three like set screws 45, have lower ends 45a engaging the top wall 11c of the transducer, thereby urging the transducer bottom wall 13 firmly against the abdomen.

The set screws have threaded shanks 45a engaging the nuts 47 integral with the base wall 14 and located above the latter. The screws project above the wall 14 and nuts 47, and have knob-like heads 45c that are individually adjustably rotatable to press different portions of the transducer downwardly relative to the base wall 14, for firm and best acoustic coupling to the abdomen, thereby to efficiently pass sound waves to the transducer. As referred to the device can be used to detect uterine muscle activities.

The set screws are spaced about the central opening 20 in the base wall 14, as shown, so as not to interfere with enlargement 11a. The nuts and set screws may also consist of lightweight, plastic material.

I claim:

1. A monitoring transducer positioning apparatus, for retention to the body of a patient, comprising
   (a) an inverted generally cup-shaped holder to receive and position the transducer, the holder including a base wall and a skirt,
   (b) first means associated with the holder to retain it to the patient's body, and
   (c) second means on the holder to urge the transducer toward the patient's body, relative to the holder, said second means including multiple set screws projecting through said base wall, said screws having ends positioned below said base wall in sidewardly spaced relation to the skirt to be directly engagable with the transducer at multiple locations, said screws having heads located above said base wall for manipulation to rotate the screws relative to the holder and transducer.

2. The apparatus of claim 1 wherein said first means includes flange means projecting from the holder, and adapted to removably connect to retainer means that has an adhesive surface applicable to the patient's body.

3. The apparatus of claim 2 including said retainer means in the form of a pad having a first portion connectible to the flange means and a second portion defining said adhesive surface.

4. The apparatus of claim 3 wherein said first portion of the pad defines another adhesive surface adhered to the flange means.

5. The apparatus of claim 2 wherein said flange means includes two flanges extending generally oppositely from skirt sections defined by said holder, said flanges angled to fit the curvature of a pregnant patient's abdomen.

6. The apparatus of claim 5 including said retainer means in the form of two pads, the pads having first portions connectible to the respective flanges, and second portions defining adhesive surfaces applicable to a patient's body.

7. The apparatus of claim 6 wherein the flanges and the pad first portions have tongue and groove interconnection allowing the pads to be lifted off the flanges for disconnection of the holder from the pads, while the pad second portions remain adhesively secured to the patient's body.

8. The apparatus of claim 1 wherein said screws project into a recess defined by the holder base wall and skirt, for urging the transducer away from the base wall and toward the patient's body.

9. The apparatus of claim 8 wherein there are three of said set screws circularly spaced apart and with ends engagable with the transducer at three locations.

10. The apparatus of claim 9 including threaded openings carried by the base wall for threaded reception of the adjustable set screws.

11. The apparatus of claim 10 wherein the set screws are carried by the base wall, and pass through it to extend beneath the base wall for engagement with the transducer.

12. The apparatus of claim 1 including nuts on the base wall, in threaded engagement with set screws threaded shanks.

13. The apparatus of claim 11 wherein the base wall defines a central through opening, and the set screws are spaced about that opening.

14. The apparatus of claim 10 wherein the base wall and skirt means consist of thin, plastic material, and there are stiffener webs interconnecting the skirt sections and base, at edges thereof.

* * * * *